United States Patent
Velamakanni et al.

(10) Patent No.: US 9,044,292 B2
(45) Date of Patent: Jun. 2, 2015

(54) DENTAL ARTICLES INCLUDING A CERAMIC AND MICROPARTICLE COATING AND METHOD OF MAKING THE SAME

(75) Inventors: Bhaskar V. Velamakanni, Woodbury, MN (US); Todd D. Jones, St. Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 13/814,962

(22) PCT Filed: Aug. 8, 2011

(86) PCT No.: PCT/US2011/046923
§ 371 (c)(1),
(2), (4) Date: Feb. 8, 2013

(87) PCT Pub. No.: WO2012/027091
PCT Pub. Date: Mar. 1, 2012

(65) Prior Publication Data
US 2013/0137065 A1    May 30, 2013

Related U.S. Application Data

(60) Provisional application No. 61/372,784, filed on Aug. 11, 2010.

(51) Int. Cl.
*A61C 5/10* (2006.01)
*A61C 5/08* (2006.01)
*A61C 13/09* (2006.01)
(Continued)

(52) U.S. Cl.
CPC ... *A61C 5/10* (2013.01); *A61C 5/08* (2013.01); *A61C 13/0003* (2013.01); *A61C 13/09* (2013.01); *A61K 6/0008* (2013.01); *A61K 6/0017* (2013.01); *A61K 6/0094* (2013.01); *A61K 6/024* (2013.01); *A61K 6/025* (2013.01)

(58) Field of Classification Search
CPC .................................... A61C 5/10; A61C 5/08
USPC .................... 433/202.1–204, 212.1, 218–223
See application file for complete search history.

(56) References Cited

U.S. PATENT DOCUMENTS 4,104,798 A    8/1978    Takahashi
4,112,631 A    9/1978    Howard
(Continued)

FOREIGN PATENT DOCUMENTS

DE    1903935    8/1970
EP    0173567    3/1986
(Continued)

OTHER PUBLICATIONS

Castarlenas, "Allenylidene-ruthenium-arene precatalyst for ring opening metathesis polymerisation (ROMP)", Journal of Organometallic Chemistry, Dec. 2002, vol. 663, No. 1, pp. 235-238.
(Continued)

*Primary Examiner* — Ralph Lewis
(74) *Attorney, Agent, or Firm* — 3M Innovative Properties Company; Qiang Han (57) ABSTRACT

Provided are methods of improving the wear resistance and aesthetic properties of dental articles though use of ceramics and microparticles, as well as dental articles having an abrasion resistant microparticle and ceramic coating thereon.

9 Claims, 3 Drawing Sheets

(51) Int. Cl.
*A61K 6/00* (2006.01)
*A61K 6/02* (2006.01)
*A61C 13/00* (2006.01)

(56) References Cited

U.S. PATENT DOCUMENTS

| | | | |
|---|---|---|---|
| 4,259,075 A | 3/1981 | Yamauchi | |
| 4,294,349 A * | 10/1981 | Ibsen et al. | 206/63.5 |
| 4,298,738 A | 11/1981 | Lechtken | |
| 4,324,744 A | 4/1982 | Lechtken | |
| 4,356,296 A | 10/1982 | Griffith | |
| 4,364,731 A | 12/1982 | Norling | |
| 4,385,109 A | 5/1983 | Lechtken | |
| 4,499,251 A | 2/1985 | Omura | |
| 4,503,169 A | 3/1985 | Randklev | |
| 4,537,940 A | 8/1985 | Omura | |
| 4,539,382 A | 9/1985 | Omura | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,695,251 A | 9/1987 | Randklev | |
| 4,710,523 A | 12/1987 | Lechtken | |
| 4,722,689 A | 2/1988 | Corbett | |
| 4,737,593 A | 4/1988 | Ellrich | |
| 4,752,338 A | 6/1988 | Reiners | |
| 4,872,936 A | 10/1989 | Engelbrecht | |
| 5,011,410 A | 4/1991 | Culler | |
| 5,024,711 A | 6/1991 | Gasser | |
| 5,026,902 A | 6/1991 | Fock | |
| 5,076,844 A | 12/1991 | Fock | |
| 5,130,347 A | 7/1992 | Mitra | |
| 5,154,762 A | 10/1992 | Mitra | |
| 5,210,109 A | 5/1993 | Tateosian | |
| 5,276,068 A | 1/1994 | Waknine | |
| 5,288,230 A | 2/1994 | Nikutowski | |
| 5,308,243 A * | 5/1994 | Emmons | 433/203.1 |
| 5,454,716 A | 10/1995 | Banerjee | |
| 5,501,727 A | 3/1996 | Wang | |
| 5,530,038 A | 6/1996 | Yamamoto | |
| 5,545,676 A | 8/1996 | Palazzotto | |
| 5,624,261 A | 4/1997 | Wiedenfeld | |
| 6,001,909 A | 12/1999 | Setiabudi | |
| 6,030,606 A | 2/2000 | Holmes | |
| 6,040,044 A | 3/2000 | Takahashi | |
| 6,095,809 A | 8/2000 | Kelly | |
| 6,106,295 A | 8/2000 | Wilson | |
| 6,218,100 B1 | 4/2001 | Wollowitz | |
| 6,251,963 B1 | 6/2001 | Kohler | |
| 6,291,078 B1 | 9/2001 | Chen | |
| 6,387,981 B1 | 5/2002 | Zhang | |
| 6,458,868 B1 | 10/2002 | Okada | |
| 6,572,693 B1 | 6/2003 | Wu | |
| 6,696,157 B1 | 2/2004 | David | |
| 6,730,156 B1 | 5/2004 | Windisch | |
| 6,730,353 B2 | 5/2004 | Robinson | |
| 6,765,036 B2 | 7/2004 | Dede | |
| 6,843,654 B1 | 1/2005 | Liu | |
| 6,852,768 B2 | 2/2005 | Jin | |
| 7,008,229 B2 | 3/2006 | Stoller | |
| 7,090,721 B2 | 8/2006 | Craig | |
| 7,091,259 B2 | 8/2006 | Bui | |
| 7,189,429 B2 | 3/2007 | Robinson | |
| 7,214,262 B2 * | 5/2007 | Hurwitz et al. | 106/35 |
| 7,261,925 B2 | 8/2007 | Nesbitt | |
| 7,838,082 B2 | 11/2010 | Nesbitt | |
| 7,927,538 B2 | 4/2011 | Moszner | |
| 2003/0166740 A1 | 9/2003 | Mitra | |
| 2003/0194681 A1 | 10/2003 | Stoller | |
| 2003/0195273 A1 | 10/2003 | Mitra | |
| 2004/0121291 A1 | 6/2004 | Knapp | |
| 2004/0215313 A1 | 10/2004 | Cheng | |
| 2005/0048445 A1 * | 3/2005 | Ito | 433/219 |
| 2005/0124762 A1 | 6/2005 | Cohen | |
| 2006/0257824 A1 * | 11/2006 | Pfeiffer et al. | 433/218 |
| 2007/0248927 A1 | 10/2007 | Luchterhandt | |
| 2008/0160193 A1 | 7/2008 | Mitchell | |
| 2008/0182114 A1 | 7/2008 | Kim | |
| 2008/0293846 A1 | 11/2008 | Craig | |
| 2008/0318189 A1 | 12/2008 | Brodkinn | |
| 2009/0061895 A1 | 3/2009 | Vasa | |
| 2009/0075239 A1 | 3/2009 | Abuelyaman | |
| 2009/0088494 A1 | 4/2009 | Luchterhandt | |
| 2009/0286205 A1 | 11/2009 | Johnson | |
| 2010/0078806 A1 | 4/2010 | Chakrapani | |
| 2010/0249305 A1 | 9/2010 | Laubersheimer | |
| 2013/0130203 A1 | 5/2013 | Velamakanni | |
| 2013/0137064 A1 | 5/2013 | Velamakanni | |
| 2013/0137065 A1 | 5/2013 | Velamakanni | |

FOREIGN PATENT DOCUMENTS

| | | |
|---|---|---|
| EP | 712622 | 9/1999 |
| EP | 1051961 | 2/2006 |
| GB | 1115544 | 5/1968 |
| GB | 1124645 | 8/1968 |
| JP | 1277553 | 11/1989 |
| JP | 2002-226316 | 8/2002 |
| RU | 2223066 | 2/2004 |
| WO | WO 00-38619 | 7/2000 |
| WO | WO 00-42092 | 7/2000 |
| WO | WO 01-07444 | 2/2001 |
| WO | WO 01-30305 | 5/2001 |
| WO | WO 01-30306 | 5/2001 |
| WO | WO 01-30307 | 5/2001 |
| WO | WO 01-92271 | 12/2001 |
| WO | WO 03-063804 | 8/2003 |
| WO | WO 2005-032392 | 4/2005 |
| WO | WO 2006-127196 | 11/2006 |
| WO | WO 2007-028787 | 3/2007 |
| WO | WO 2011-017113 | 2/2011 |
| WO | WO 2012-021434 | 2/2012 |
| WO | WO 2012-021442 | 2/2012 |
| WO | WO 2012-027091 | 3/2012 |

OTHER PUBLICATIONS

Delong, "The Development of an Artificial Oral Environment of Testing of Restoratives", J. Dental Research, 1983, No. 62, pp. 32-36.
Hafner, "One-Component Catalysts for Thermal and Photoinduced Ring Opening Matathesis Polymerization", Angew. Chem. Int., 1997, vol. 36, No. 19, pp. 2121-2124.
Pallav, "Wear Rates of Composites, an amalgam, and enamel under stress-bearing conditions", J. Pros. Dent. Apr. 1988, vol. 59, No. 4, pp. 426-429.
International Search Report for PCT International Application No. PCT/US2011/046915 Mailed Nov. 4, 2011, 3 pages.

* cited by examiner

DENTAL ARTICLES INCLUDING A CERAMIC AND MICROPARTICLE COATING AND METHOD OF MAKING THE SAME

CROSS REFERENCE TO RELATED APPLICATIONS

This application is a national stage filing under 35 U.S.C. 371 of International Application No. PCT/US2011/0469203 filed Aug. 8, 2011, which claims priority to U.S. Provisional Application No. 61/372,784, filed Aug. 11, 2010. The disclosures of both applications are incorporated by reference in their entirety herein.

BACKGROUND

Flexible metal articles are desirable for treatment of a variety of dental maladies. Such articles have proven reasonably durable over both short-term and long-term dental treatment. Dental articles made from or including a malleable metal substrate may typically be modified chair side to adapt to the tooth structures of a particular patient and ensure a secure installation. This degree of post-manufacturing freedom has made malleable metal especially popular as dental crowns and orthodontic bands.

Metal crowns, particularly those made of stainless steel are well suited for children, as their reasonable life span coincides with the natural loss of children's teeth. The metallic sheen of stainless steel, however, is not exactly aesthetically appealing. Accordingly, attempts have been made to apply aesthetic coatings to stainless steel crowns, but these efforts have experienced little success in maintaining flexibility and durability.

SUMMARY

Stainless steel and most other untreated or uncoated metals have become increasingly unappealing to patients desiring high-quality aesthetics in addition to high performance and durability. Accordingly, there is an increased demand for dental articles that match or mimic the natural color of teeth. Attempts to meet this demand, including coating with polymer resins, have been thus far been less than desirable. In some prior art solutions, the coating does not sufficiently adhere to the surface during the entirety of treatment or the coating becomes easily stained upon exposure to food. In other prior art solutions, the required coating is so thick that the crown may not be freely manipulated without cracking, potentially requiring substantial removal of the tooth structure for seating the crown. Such substantial removal may lead to increased patient sensitivity and other complications.

The dental articles of the present disclosure include an abrasion resistant hybrid coating on at least a portion of the article's outer surface. The abrasion resistant coating of the present disclosure exhibits improved wear and stain resistance while maintaining aesthetic appeal during the full period of treatment. The coating of the present disclosure further provides a smooth outer surface for the dental article, reducing patient discomfort upon tongue or lip contact.

Unlike previous aesthetic dental articles, the abrasion resistant hybrid coated dental articles maintain desired flexibility such that they may be cut, bent, crimped, or otherwise manipulated by a practitioner without delamination or other failure. Therefore, use of the coated dental articles may allow a dental or orthodontic practitioner to precisely modify the fit or shape of the dental article without sacrificing performance or appearance.

Abrasion resistant hybrid coated dental articles of the present disclosure may be crimped and/or otherwise manipulated without deleteriously affecting the aesthetics or performance of the coating. The coating is desirably sufficiently thin on the outer surface so as to be pliable enough to undergo manipulation without damage or failure. Preferably, the coating is also sufficiently thick in order to withstand typical mastication (i.e., chewing) and oral preventive care (e.g., brushing) forces throughout the life of the article. The abrasion resistant hybrid coating includes a ceramic material, a hardenable dental composition, and a plurality of spherical microparticles.

As used herein, the term "hardenable" refers to a material that can be cured or solidified, e.g., by heating to remove solvent, heating to cause polymerization, chemical crosslinking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "dental article" means an article that can be adhered (e.g., bonded) to an oral surface (e.g., a tooth structure). Examples include, but are not limited to, replacements, inlays, onlays, veneers, full and partial crowns (both temporary and permanent), bridges, implants, implant abutments, copings, dentures, posts, bridge frameworks and other bridge structures, abutments, orthodontic appliances and devices including, but not limited to archwires, buccal tubes, brackets and bands, and prostheses (e.g., partial or full dentures).

As used herein, the term "ethylenically unsaturated compound" is meant to include monomers, oligomers, and polymers having at least one ethylenic unsaturation.

As used herein, the term "nanofiller" means a filler having an average primary particle size of at most 200 nanometers. The nanofiller component may be a single nanofiller or a combination of nanofillers.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

As used herein, "phosphorylated monomer" refers to a monomer (e.g., a (meth)acrylate) that comprises at least one phosphate or phosphonate group.

As used herein, the term "thermal initiator" means a species capable of efficiently inducing or causing polymerization or crosslinking by exposure to heat.

As used herein, "occlusal" means in a direction toward the outer tips of the patient's teeth.

As used herein, "gingival" means in a direction toward the patient's gums or gingiva.

As used herein, "proximal surface" means the surface nearest to the adjacent tooth.

As used herein, "interproximal" means between the proximal surfaces of adjoining teeth.

As used herein, "anterior crown" means a crown intended to replace incisor and canine teeth.

As used herein, "continuous" means extending substantially across a target surface and including no deliberate gaps or interruptions other those inherent in the material.

As used herein, "height of contour" means the point of greatest convexity of a tooth or crown.

As used herein, deposited or disposed "substantially above the height of contour" and variations mean little to no coating is deliberately deposited the below the height of contour.

As used in the claims, "filler" means nanofiller, other filler, and combinations thereof.

As used herein, "average microparticle diameter" and variations thereof refers to the size of about 50 percent or more of the microparticles in the coating.

As used herein, "a," "an," "the," "at least one," and "one or more" are used interchangeably. Thus, for example, a hardenable composition that comprises "a" flexible monomer can be interpreted to mean that the hardenable composition includes "one or more" flexible monomers.

As recited herein, all numbers should be considered modified by the term "about".

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

BRIEF DESCRIPTION OF THE DRAWINGS

The invention will be further described with reference to the drawings, wherein corresponding reference characters indicate corresponding parts throughout the several views, and wherein.

Layers in the depicted embodiments are for illustrative purposes only and are not intended to define the thickness, relative or otherwise, or the location of any component.

DETAILED DESCRIPTION OF ILLUSTRATIVE EMBODIMENTS

The dental articles of the present disclosure include an abrasion resistant hybrid coating on at least a portion of the article's outer surface. The abrasion resistant hybrid coatings of the present disclosure exhibits improved wear and stain resistance while maintaining aesthetic appeal during the full period of treatment. Unlike previous aesthetic dental articles, the abrasion resistant hybrid coated dental articles maintain desired flexibility such that they may be cut, bent, crimped, or otherwise manipulated by a practitioner without delamination or other failure. Therefore, use of the coated dental articles allows a dental or orthodontic practitioner to precisely modify the fit or shape of the dental article without sacrificing performance or appearance.

Figure 1:
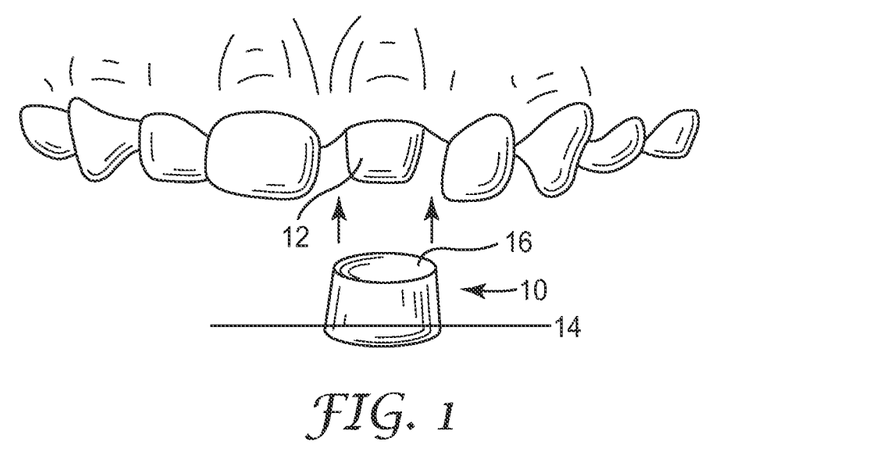
FIG. 1 is a perspective view of a stainless steel crown.

A coated dental article according to one embodiment of the present disclosure is a stainless steel crown (SSC). A typical SSC is constructed from a preformed base material crown 10 composed of stainless steel, which is placed in the mouth to cover a prepared tooth 12 as shown in FIG. 1. The prepared tooth 12 is shown as having its surface ground away sufficient for the placement of the crown 10 thereon. The scale of the teeth shown and the crown 10 to be placed thereon is for ease of illustration and should not be considered to be at the correct scale. Furthermore, the portion of the tooth 12, which has been ground away, is also for illustration purposes only. As shown in FIG. 1, the base metal crown 10, which as shown for illustration purposes, is not a molar, and therefore can be pictured generally as a flattened bowl which is formed in the shape of a tooth with an open end 16 for placement over the prepared tooth 12. Proper tooth preparation includes removing all caries and proper shaping of the remaining natural tooth 12 to receive the SSC 10. Therefore, the prepared tooth 12 is typically left in place in the mouth so that its root provides anchor in the jaw for the SSC 10. The SSC 10 shown in FIG. 1 is an anterior crown; however, it is to be understood that the present disclosure is applicable to both anterior and to posterior crowns as well.

Typically an SSC is shaped to resemble the tooth that it replaces and is sized to fit comfortably over the portion of the tooth on which the dental procedure is being performed. The crown is trimmed so that the bottom edge of the crown meets the gum line in a comfortable manner approximating the placement of the tooth when the crown is applied. The crowns are manufactured in sizes and shapes to fit the various types of teeth. The stainless steel is preferably malleable so it can be crimped around the base of the tooth and shaped on the occlusal surface to provide a comfortable bite with the opposing tooth. Precise adjustments by a practitioner to the shape and/or size the SSC are often, though not always, made to the portion of the SSC below the height of contour 14.

Commercially available preformed stainless steel crowns can be obtained from 3M Company, St. Paul, Minn. Other sources of preformed stainless steel crowns include Acero XT, Dallas, Tex. and Denovo Dental, Baldwin Park, Calif.

The preformed base metal in a SSC is typically constructed of cold rolled stainless steel. Prior to coating, the crown can be prepared to remove oil or other surface contaminants by vapor degreasing, alkaline cleaning, acetone cleaning, or ultra-sonic cleaning, for example, as needed. Surface oxides may be removed and surface activation can be accomplished by acid treatment or abrasive blasting, for example, as described in more detail below.

Typical stainless steel materials used to construct stainless steel crowns useful in the present disclosure include AISI-Types 304, 305, and 316 stainless steel sheeting (based on the American Iron and Steel Institute Classification of Chromium-Nickel Stainless Steels). Such sheeting includes a metal alloy of iron, chromium, and nickel typically with small or trace amounts of manganese, carbon, titanium, aluminum, silicon, tantalum, and molybdenum.

Figure 2:
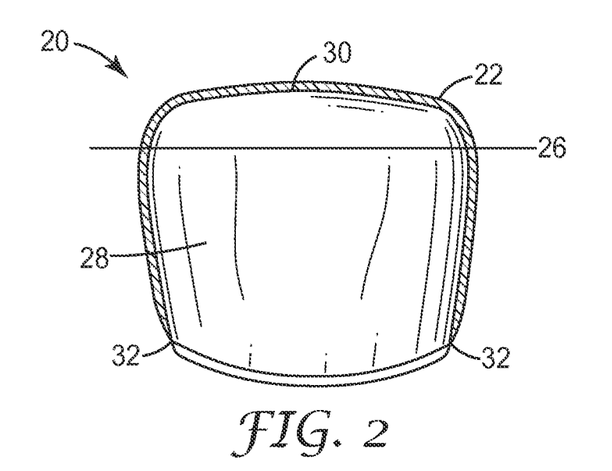
FIG. 2 is a front plan view of a coated stainless steel crown according to an embodiment of the present invention.

FIG. 2 depicts a front plan view of an aesthetic posterior SSC 20, including a abrasion resistant hybrid coating 22. The exterior of the crown includes a height of contour 26 extending across the wall surface 28 below occlusal surface 30 as it transitions into an integral circumferential area or continuous wall. In the depicted embodiment, portions of the cervical margin, including those proximate the gingival-labial and the gingival-lingual edge regions 32 may be left uncoated to allow for more precise manipulation and trimming. It is further contemplated that the entire outer surface of the SSC may be coated with the abrasion resistant hybrid coating, including the cervical margins.

Though not depicted, it is also contemplated that the coatings of the present disclosure be used on anterior crowns. In some embodiments, the entire outer surface of the anterior crown may be coated. In other embodiments, only the portion of the anterior crown coming into contact with the opposing dentition (e.g., incisal surface) or the portion above the height of contour need be coated. Other portions of an anterior crown may be coated as desired.

Figure 3:
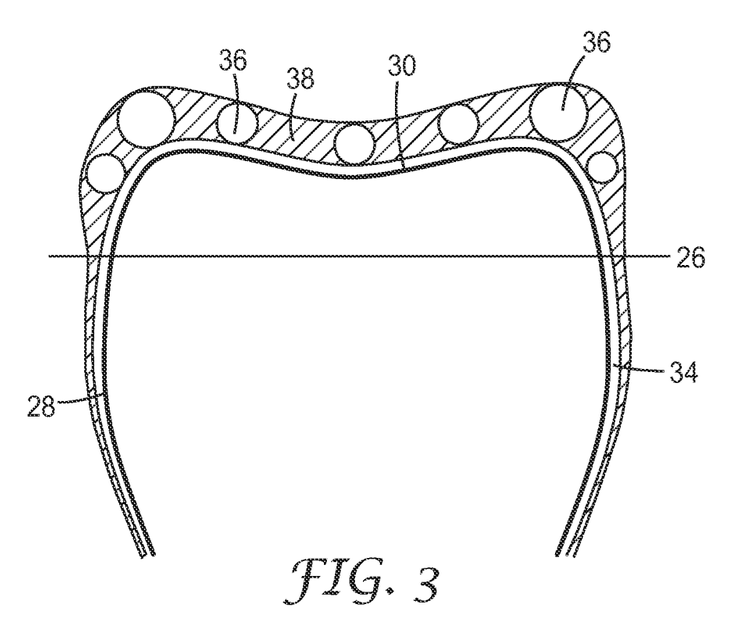
FIG. 3 is a cross-sectional view of the stainless steel crown of FIG. 2.

FIG. 3 illustrates a cross-sectional view of the coated SSC 20 of FIG. 2. The outer surface may be primed to include micro texture (e.g., abraded, deposited, or etched) according to methods described herein. A ceramic layer 34 including a ceramic material is disposed on the surface 30. As depicted in FIG. 3, the ceramic layer is continuous over the entire coated surface. The ceramic layer may be disposed on the entire outer surface of the crown, substantially above the height of contour, or some other portion of the crown. The ceramic material is directly bonded, by e.g., an intimate chemical or mechanical interaction, to the target surface.

A plurality of spherical microparticles 36 are embedded in a first polymeric layer 38. As depicted, the microparticles are distributed across the occlusal surface 30, with little to no coverage below the height of contour 26. In the depicted embodiment, at least one spherical microparticle is in close proximity to, if not intimate contact with, the ceramic layer 34. In other embodiments, one or more of the spherical microparticles may be "suspended" in one or more polymeric layers (i.e., no portion of the microparticle is in contact with the ceramic layer 34 or the outer surface of the crown).

The average microparticle is at least 20 microns in diameter, more preferably at least 30 microns, and even more preferably at least 50 microns. Furthermore, the average microparticle diameter is no greater than 300 microns, more preferably no greater than 200 microns, and even more preferably no greater than 100 microns. Microparticles having an average diameter less than 20 microns may be difficult to sufficiently distribute in a polymeric layer and may not result in sufficient wear resistance. Microparticles larger than 300 microns may require a much thicker polymeric coating, leading to potential decreases in flexibility and patient comfort.

In some embodiments, the size distribution of microparticles is narrow, in that the diameter does not differ more than 20% between microparticles. In other embodiments, the plurality of spherical microparticles includes a greater distribution of varying particle diameters. For example, the plurality of particles may comprise a mixture of particles a portion of which has an average particle diameter of 70 microns, and a portion of which has an average particle diameter of 50 microns.

The first polymeric layer 38 includes a first hardened dental composition and is disposed on a portion of outer surface of the SSC, a portion of the ceramic layer 34, and a portion of the spherical microparticles 36. As depicted in FIG. 3, the first polymeric layer 34 is continuous over the entire outer surface. As depicted in FIG. 3, both the ceramic and polymeric layers (34, 38) cover the entire outer surface of the SSC 20, with the ceramic and polymeric layers in intimate contact on the wall surfaces below the height of contour 26. It is also contemplated, though not depicted in FIG. 3, that either the ceramic layer 34 or first polymeric layer only extend across the occlusal surface 30 above the height of contour 26 or some other portion of crown surface less than the entire outer surface.

One or more additional polymeric layers are also contemplated (though not depicted), so that a coated dental article may include a plurality of polymeric layers. Suitable additional polymeric layers include those described in co-pending application entitled, POLYMER COATED DENTAL ARTICLES AND METHOD OF MAKING THE SAME, International Patent Application Number PCT/US2011/046909, filed on Aug. 8, 2011.

In some embodiments, the thickness of the coating layer is substantially consistent over the entire coated surface of the dental article. In other embodiments, the coating may include a thickness gradient. Such a gradient may include a gradual decrease or an abrupt decrease in coating thickness, or a combination thereof. For example, the thickness of the coating on the occlusal surface 30 may be greater than the thickness of the coating on the wall surfaces 28 (e.g., the interproximal surfaces) proximate the height of contour. Further, the coating thickness may then approach zero as the cervical margin is approached in a gingival direction. It is also contemplated that the thickness of the coating on the occlusal surface 30 be less than the thickness of the coating on the wall surfaces 28.

In most embodiments, the total thickness 40 of the hardened polymeric layer(s) and ceramic layer 34 on the occlusal surface is at least the average diameter of the spherical microparticles 36. While it is appreciated that the total coating thickness may be less than the average microparticle diameter in some embodiments, such coatings may be susceptible to increased wear and aesthetic degradation as the spherical microparticles are eventually removed by shear force during the act of chewing. In some embodiments, the total thickness 40 on the occlusal surface is at least twice (2×) the average microparticle diameter. In most embodiments, the total polymeric thickness is no greater than five times (5×) the average microparticle diameter. Coatings having a total polymeric thickness greater than 5× may not be sufficiently flexible for practitioner manipulation.

The ceramic layer should be sufficiently thick to ensure wear resistance and aesthetic preferences. In one embodiment, the ceramic layer is at least 10 microns thick. In a further embodiment, the ceramic layer is at least 55 microns thick. In a stainless steel crown including a thickness gradient as described above, it should be appreciated that the minimum thickness is in reference to the thickness of the ceramic layer 34 on the occlusal surface 30. In one embodiment, the thickness 20 of the ceramic layer is no greater than 150 microns. In a further embodiment, the thickness of the ceramic layer is no greater than 100 microns. In a further embodiment, the thickness of the ceramic layer is no greater than 75 microns.

In one embodiment, the thickness of the one or more polymeric layers is no less than 5 microns. In another embodiment, the thickness of the one or more polymeric layers is no less than 10 microns. In a further embodiment, the thickness of the one or more polymeric layers is no less than 20 microns. In one embodiment, the thickness of the one or more polymeric layers is no greater than 300 microns. In another embodiment, the thickness of the one or more polymeric layers is no greater than 150 microns. In a further embodiment, the thickness of the one or more polymeric layers is no greater than 50 microns.

As noted above, the thickness of the coating may approach zero on portions of the gingival or interproximal surfaces. In certain embodiments, the thickness of the coating on the wall surfaces below the height of contour is no greater than 150 microns, in other embodiments less than 100 microns, in yet other embodiments less than 50 microns. In a further embodiment, the thickness of the coating on the wall surfaces below the height of contour is no greater than 30 microns. Thicknesses exceeding 150 microns may not provide sufficient flexibility in certain embodiments.

Figure 4:
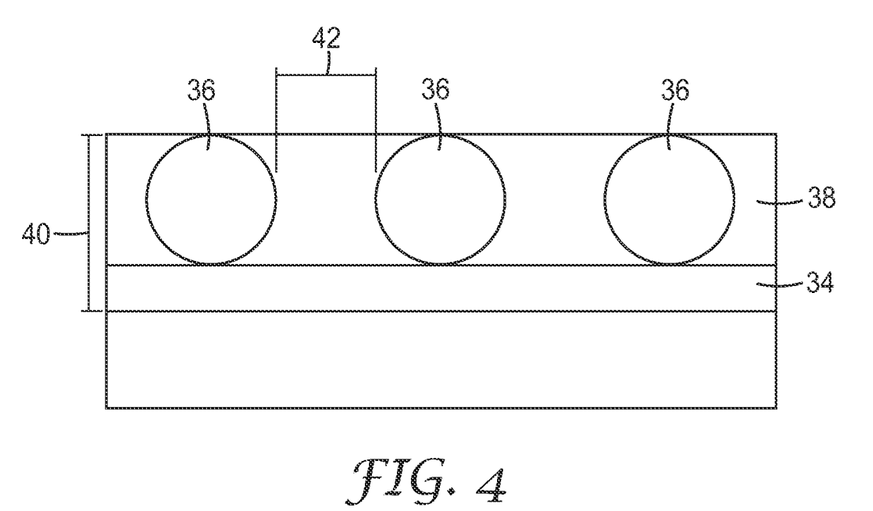
FIG. 4 is a cross-sectional view of a stainless steel crown according to an embodiment of the present disclosure.

The arrangement of the spherical microparticles may be further understood with reference to FIG. 4. As depicted, the spherical microparticles are spaced from one another, as measured on an edge to edge basis (identified in FIG. 4 by numerical indicator 42), on the order of the average diameter of the microparticles used. The average spacing may be between close packed (microparticles are touching or are nearly touching) and five times the average microparticle diameter. Though contemplated, bead spacing that approaches closely packed conditions may adversely affect the aesthetic properties of a coated crown due to the relative predominance of beads and resultant reduction in the amount/coverage of polymeric/ceramic coating. Microparticles that are too closely packed may further reduce the flexibility and polymer adhesion. In certain embodiments, the average spacing is between one quarter of the average diameter and three times the average diameter. In preferred embodiments, the average spacing is between one quarter of the average diameter and two times the average diameter.

In certain embodiments, the spacing between microparticles is substantially uniform. In other embodiments, the microparticles can be more randomly distributed.

Alternatively, from 3% by weight to 90% by weight of the microparticles are present in the coating, more preferably, from 7% to 60% by weight based on the weight of the entire coating (i.e., spherical microparticles and all ceramic and polymeric layers) in the area where beads are present.

Figure 5:
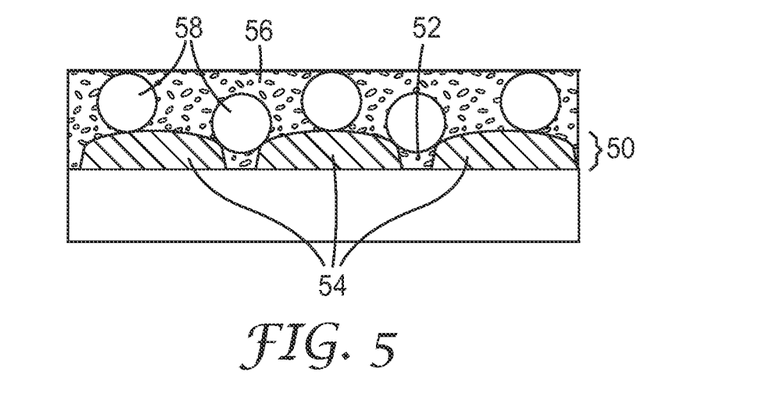
FIG. 5 is an enlarged frontal view of a cross-section of a coated stainless steel crown according to an embodiment of the present disclosure.

As noted above, the ceramic layer can be discontinuous (e.g., patterned) on the coated surface of the SSC. One embodiment of a discontinuous ceramic layer 50 on a surface is illustrated in FIG. 5. Such a discontinuous layer includes gaps 52 (i.e., pores or apertures) between deposits of ceramic material 54. In the depicted embodiment, the polymeric layer 56 (or polymeric layers) partially or completely fills the gaps 52 between the ceramic deposits 54. In some embodiments, the spherical microparticles 58 partially fill at least some of the gaps 52. In other embodiments, wherein gaps are larger than the average microparticle diameter, at least some of the microparticles may completely fill at least some of the gaps 52. Without wishing to be bound by theory, the gaps 52 in the discontinuous ceramic layer may improve appearance and flexibility, as well as improve the adhesion of the one or more polymeric layers to the dental article surface.

In some embodiments, the discontinuous ceramic layer includes an identifiable pattern of alternating gaps and ceramic deposits. In other embodiments, the ceramic layer is irregular or otherwise non-patterned (e.g., varying distances between deposits). Other embodiments may include a combination of patterned and non-patterned sections of the ceramic layer.

Figure 6:
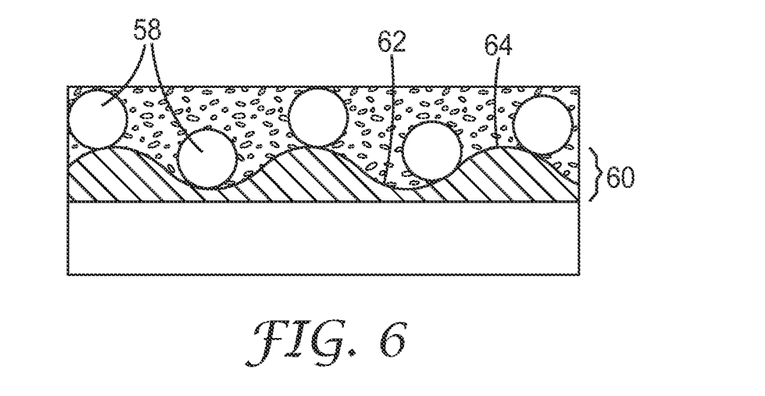
FIG. 6 is an enlarged frontal view of a cross-section of a coated stainless steel crown according to a further embodiment of the present disclosure.

It is also contemplated that the ceramic layer may be substantially continuous over at least a portion of the outer surface, but may comprise discrete ceramic sections of varying thickness. Such an embodiment is depicted in FIG. 6. The ceramic layer 60 includes apparent peaks 64 and valleys 62. The valleys 62 (i.e., areas of the surface have a thinner coating section) may be sufficiently thin so as to enable flexibility of the overall construction. In one embodiment, the pitch of the structured ceramic surface (i.e. the distance between repeating peaks 64) may be on a length-scale such that it is not readily visible to the unassisted eye. Accordingly, the pitch in one embodiment is 0.2 mm, in another embodiment 0.1 mm, and in a further embodiment 0.05 mm. Furthermore, the ratio of the area of the valleys 62 to the area of the peaks 50 in the structured surface in one embodiment may be at least 0.3, in another embodiment at least 0.5 and in a further embodiment at least 0.7.

Without wishing to be bound by theory, a hardenable composition of the one or more polymeric layers may penetrate openings in continuous (e.g., micropores) and discontinuous layers form an interpenetrating network (IPN).

Suitable ceramic materials for use in a ceramic layer include, but are not limited to, alumina, zirconia, yttria, yttria-stabilized zirconia, porcelain, blends and other combinations thereof.

In certain embodiments, the spherical microparticles include an inorganic material. Suitable materials for use as inorganic spherical microparticles include ceramics and glass-ceramics. Suitable materials for use as inorganic spherical microparticles include, but are not limited to, alumina, zirconia, yttria, yttria-stabilized zirconia, porcelain, blends and other combinations thereof. Particularly useful yttria-stabilized zirconia spherical microparticles are available from Glen Mills, Inc., Clifton, N.J.

Exemplary hardenable compositions useful for creating the one or more polymeric layers include at least one of a polymerizable component, an initiator system, a pigment, a nanofiller, a filler, and other additives (e.g., solvents). Particularly useful hardenable dental compositions exhibit a color similar to a patient's tooth (e.g., ivory) when deposited on the surface of the dental article, either alone or in cooperation with other hardenable dental compositions. The potential components of the hardenable composition are described in more detail below.

Polymerizable Component

The hardenable compositions of the present disclosure are typically hardenable due the presence of a polymerizable component. In some embodiments, the compositions can be hardened (e.g., polymerized by conventional photopolymerization and/or chemical polymerization techniques) after it has been applied to the surface of a dental article.

In certain embodiments, the compositions are photopolymerizable, i.e., the compositions contain a photoinitiator system that upon irradiation with actinic radiation initiates the polymerization (or hardening) of the composition. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions.

In other embodiments, the compositions are thermally polymerizable, i.e., the compositions contain a thermal initiator system that upon heating or other application of thermal energy initiates the polymerization (or hardening) of the composition.

The polymerizable component typically comprises one or more ethylenically unsaturated compounds, with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof. The polymerizable component may comprise one or more ethylenically unsaturated compounds, with or without acid functionality that is phosphorylated, such as a phosphorylated methacrylate.

The compositions, especially in photopolymerizable implementations, may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth) acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone(meth)acrylamide; urethane(meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also comprise monomers that are curable by ring-opening metathesis polymerization (ROMP) having at least one functionality curable by ROMP, such as at least one endocyclic olefinically unsaturated doublebond. Generally, suitable monomers can follow the general formula $B-A_n$ wherein A is a moiety polymerizable by ROMP such as cyclobutenyl, cyclopentenyl, cyclooctenyl or bicyclic ring systems like the often preferred norbornenyl and 7-oxa-norbornenyl groups, and B is an organic or silicon-organic backbone with 1 to 100, e.g., 1 to 10 or 1 to 5 or 1 to 4 moieties polymerizable by ROMP, e.g., 2 or 3 moieties polymerizable by ROMP, are attached, n being 1 to 100. The composition according to the disclosure may contain only one type of monomer according to the general formula B-A. It is also possible that a composition according to the disclosure contains two or more different types of monomers according to the general formula B-A. In some embodiments, the composition contains at least one type of monomer according to the general formula $B-A_n$, which has one or two olefinically unsaturated double bonds which are curable by ROMP. Suitable monomers are described, for example, in great detail in US Patent Publication No. 2009/00884 (Luchterhandt et al.).

The polymerizable component may also contain hydroxyl groups and ethylenically unsaturated groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis [4-(2-hydroxy-3-methacryloxypropoxy)phenyl]propane (bisGMA). Suitable ethylenically unsaturated compounds are available from a wide variety of commercial sources, such as Sigma-Aldrich, St. Louis. Mixtures of ethylenically unsaturated compounds can be used if desired.

In certain embodiments, the polymerizable component may include, bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), phenoxyethylmethacrylate, and/or NPGDMA (neopentylglycol dimethacrylate). The polymerizable component may include combinations of these hardenable components.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth) acrylate (e.g., HEMA) phosphates, bis((meth)acryloxyethyl) phosphate, ((meth)acryloxypropyl)phosphate, bis((meth) acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components in the hardenable component system. Also monomers, oligomers, and polymers of unsaturated carbonic acids such as (meth) acrylic acids, aromatic (meth)acrylated acids (e.g., methacrylated trimellitic acids), and anhydrides thereof can be used. Certain embodiments of the composition of the present disclosure include an ethylenically unsaturated compound with acid functionality having at least one P—OH moiety.

Certain of these compounds are obtained, for example, as reaction products between isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Patent Application Publication No. 2009-0075239 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S.

Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present disclosure can also include combinations of ethylenically unsaturated compounds with acid functionality as described, for example, in U.S. Patent Application Publication No. 2007/0248927 (Luchterhandt et al.)f. The compositions may also include a mixture of ethylenically unsaturated compounds both with and without acid functionality.

Polymerizable components may also include monomers and multimethacrylate oligomers, including but not limited to, trimethylcyclohexylmethacrylate, C8-C18 monomethacrylates, phenoxyethylmethacrylate, PEGDMA (polyethyleneglycol dimethacrylate having a molecular weight of approximately 400), aliphatic urethane methacrylates, aliphatic polyester urethane methacrylates, aliphatic polyester triurethane acrylates. Further contemplated are reactions products of polytetramethylene ether diols and/or polycaprolactone polyols with isocyanatoethylmethacrylate. In certain embodiments, the flexible monomers and/or oligomers have a glass transition temperature of no greater than 60 degrees Celsius.

Adding the flexible monomers and multimethacrylate oligomers to a hardenable composition can create a composition having improved flexibility as evidenced by, for example, having at least a 3% elongation to break or ability to bend around at least an 8 mm mandrel. In certain preferred embodiments, the hardenable compositions deposited on wall surfaces below the height of contour include a flexible monomer or oligomer.

An exemplary self-cure system comprising aliphatic polyisocyanates is described in U.S. Pat. Nos. 7,189,429 and 6,730,353 (Robinson). The first part of this two-part system includes one or more aliphatic polyisocyanates. Suitable polyisocyanates include derivatives of hexamethylene-1,6-diisocyanate; 2,2,4-trimethylhexamethylene diisocyanate; isophorone diisocyanate; and 4,4'dicyclohexylmethane diisocyanate. Preferred polyisocyanates are the uretdione, biuret and isocyanurate trimer of hexamethylene-1,6-diisocyanate, with the uretdione being particularly preferred.

The preferred polyisocyanates have an isocyanate content of 15 to 30%, with an isocyanate content of 20 to 25% being particularly preferred. The aliphatic polyisocyanates may further be blended with one or more amine reactive resins and/or non-reactive resins.

The second part of a two-part coating system comprises one or more polyamines. The one or more polyamines are preferably aromatic. Suitable polyamines include diethyl toluenediamine; dimethylthio toluenediamine; 4,4'-methylenebis(2-isopropyl-6-methylaniline); and 4,4'-methylenebis(3-chloro-2,6-diethylaniline). The polyamines may further be blended with polyhydric alcohol. The polyhydric alcohol compounds can be polyester or polyether polyols containing at least two hydroxyl groups per molecule. Branched polyether-esters are particularly useful.

In another embodiment of the two-part coating system, the aromatic polyamines may be blended with oligomeric polyamines. Suitable compounds include poly(oxypropylene)diamines, poly(oxypropylene)triamines, poly(oxytetramethylene)-di-p-aminobenzoates.

Additional flexible components suitable for use in certain two-part systems include polyTHF, polyethyleneoxide, and polypropylene oxide.

Initiator Systems

In certain embodiments, the hardenable compositions of the present disclosure are photopolymerizable, i.e., the hardenable compositions contain a photopolymerizable component and a photoinitiator system that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Suitable phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl)phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the unfilled composition.

Tertiary amine reducing agents may be used in combination with an acylphosphine oxide. Illustrative tertiary amines useful in the disclosure include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the unfilled composition. Useful amounts of other initiators are well known to those of skill in the art.

In certain embodiments, the compositions of the present disclosure are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions.

In embodiments wherein the hardenable composition includes a monomer or oligomer curable by ROMP, suitable initiators include all substances which are able to initiate a ROMP polymerization in a curable composition. It is preferred that a polymer composition comprising an ROMP initiator is sufficiently chemically stable at ambient temperature, generally at room temperature or temperatures up to 60° C., providing unhindered preparation and molding of the formulation.

Suitable chemically stable initiators do not lead to an increase of viscosity of the composition of more than 10% during a minimum of 5 hours at temperatures below 50° C. It is also preferred that a suitable initiator will cure the formulation within 24 hours at a temperature above 100° C. by ROMP reaction. Preferred initiators are metal complexes of ruthenium or osmium not bearing a carbene function. Examples of suitable initiators can be found in Castarlenas et al., Journal of Organometallic Chemistr, 663 (2002) 235-238 and in Hafner et al., Angew. Chem. 1997, 109, Nr. 19, S. 2213. Further preferred initiators are disclosed in U.S. Pat. No. 6,001,909 (Setiabudi) and US Patent Publication No. 2009/00884 (Luchterhandt et al.).

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present disclosure are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight (including water) of the components of the composition. Typically, the reducing agent is present in an amount of no greater than 10% by weight, and more typically no greater than 5% by weight, based on the total weight (including water) of the components of the unfilled composition.

Typically, the oxidizing agent, if used at all, is present in an amount of at least 0.01% by weight, and more typically at least 0.10% by weight, based on the total weight (including water) of the components of the composition. Typically, the oxidizing agent is present in an amount of no greater than 10% by weight, and more typically no greater than 5% by weight, based on the total weight (including water) of the components of the unfilled composition.

The reducing or oxidizing agents can be microencapsulated as described in U.S. Pat. No. 5,154,762 (Mitra et al.). This will generally enhance shelf stability of the composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an fluoro-aluminosilicate (FAS) glass and water and maintained in a storage-stable state.

A redox cure system can be combined with other cure systems, including photoinitiator systems or with a composition such as described U.S. Pat. No. 5,154,762 (Mitra et al.).

In another embodiment of the present disclosure, the initiator system comprises free radical-generating thermal initiators. Thermal initiators include organic peroxides (e.g., benzoyl peroxide), azo compounds, quinones, nitroso compounds, acyl halides, hydrazones, mercapto compounds, pyrylium compounds, imidazoles, chlorotriazines, benzoin, benzoin alkyl ethers, diketones, phenones, and mixtures thereof. Examples of suitable thermal initiators are VAZO 52, VAZO 64 and VAZO 67 azo compound thermal initiators, all available from DuPont. Preferred thermal initiators include benzoyl peroxide, dicumylperoxide, and andazobisisobutyronitrile (AIBN).

Nanofiller

The hardenable compositions of the disclosure can be formulated with one or more nanofillers that may impart desirable wear and aesthetic properties (e.g., tooth like color to mask the underlying metal). Suitable nanofillers include either acid reactive or non-acid reactive nanofillers and may include, but are not limited to silica; zirconia; oxides of titanium, aluminum, cerium, tin, yttrium, strontium, barium, lanthanum, zinc, ytterbium, bismuth, iron, and antimony; and combinations thereof. More typical nanofillers may include zirconia ($ZrO_2$); oxides of titanium (e.g., $TiO_2$), and oxides of yttrium (e.g., $Y_2O_3$); and other metal oxides with high refractive indices. In preferred embodiments, the nanofiller comprises an oxide of titanium. As used herein, "high refractive index" means a refractive index of typically at least 1.5, and more typically of at least 2.0. Titania and zirconia are particularly useful nanofillers, as they have very high refractive indices, and will require less weight of material than a lower refractive index material to match the refractive indices appropriately.

The nanofillers typically have an average particle size of at most 100 nanometers and more typically at most 50 nanometers. Such nanofillers typically have an average particle size of at least 2 nanometers, more typically at least 5 nanometers, and even more typically at least 10 nanometers. In some embodiments, the nanofiller is in the form of nanoclusters, typically at least 80 percent by weight nanoclusters. In other embodiments, the nanofiller is in the form of a combination of nanoparticles and nanoclusters. Often a portion of the surface of the nanofiller is silane treated or otherwise chemically treated to provide one or more desired physical properties. Additional suitable nanofillers are disclosed in U.S. Pat. No. 6,387,981 (Zhang et al.) and U.S. Pat. No. 6,572,693 (Wu et al.), U.S. Publication No. 2008/0293846 (Craig et al.), as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof.

Typically, the nanofillers of the present disclosure are non-pyrogenic fillers, however pyrogenic fillers can be added as optional additives to the dental compositions.

The amount of nanofiller should be sufficient to provide a hardenable composition having desirable mixing and handling properties before hardening and good physical and optical properties after hardening. Typically, the nanofiller represents at least 0.1 wt-%, more typically at least 5 wt-% or 10 wt-%, and most typically at least 20 wt-% based on the total weight of the composition. Typically, the nanofiller represents at most 60 wt-%, more typically at most 50 wt-%, and most typically at most 40 wt-%, based on the total weight of the composition.

Pigments & Other Fillers

The hardenable compositions of the present disclosure may further include pigments. A tooth-colored pigment can be achieved, for example, by using a mixture of titanium dioxide and iron oxide. The titanium dioxide and iron oxide pigments can be used in varying amounts depending on the shade of tooth enamel desired to be reproduced. For example, 15 wt-% to 55 wt-% titanium dioxide, and 0.01 wt-% to 4.5 wt-% iron oxide, based on the total weight of the hardenable composition, give a natural tooth enamel appearance to the coating. Additional pigments or colorants can be optionally added to the starting coating powders to color-match the polymeric coating to a desired tooth color.

In addition to the nanofiller and pigment components, the hardenable compositions of the present disclosure can also optionally include one or more other fillers. Such fillers may be selected from one or more of a wide variety of materials suitable for the use in dental and/or orthodontic compositions.

The other filler can be an inorganic material. It can also be a crosslinked organic material that is insoluble in the resin component of the composition, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and silica particles (e.g., submicron pyrogenic silicas such as those available under the trade designations AEROSIL, including "OX 50," "130," "150" and "200" silicas from Degussa AG, Hanau, Germany and CAB-O-SIL M5 and TS 720 silica from Cabot Corp., Tuscola, Ill.). Examples of suitable organic filler particles include filled or unfilled pulverized polycarbonates, polyepoxides, and the like.

Suitable non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent. Suitable coupling agents include gamma-methacryloxypropyltrimethoxysilane, gamma-mercaptopropyltriethoxysilane, gamma-aminopropyltrimethoxysilane, and the like. Examples of useful silane coupling agents are those available from Crompton Corporation, Naugatuck, Conn., as SILQUEST A-174 and SILQUEST A-1230. For some embodiments of the present disclosure that include other fillers the compositions may include at least 1% by weight, more preferably at least 2% by weight, and most preferably at least 5% by weight other filler, based on the total weight of the composition. For such embodiments, compositions of the present disclosure preferably include at most 75% by weight, more preferably at most 65% by weight, and even more preferably at most 55% by weight other filler, based on the total weight of the composition.

When the polymer composition contains an ethylenically unsaturated compound and at least one filler, it is generally present in an amount of at least 15% by weight, more typically at least 25% by weight, and most typically at least 35% by weight ethylenically unsaturated compounds, based on the total weight of the filled composition. The compositions of the present disclosure typically include at most 95% by weight, more typically at most 90% by weight, and most typically at most 80% by weight ethylenically unsaturated compounds, based on the total weight of the filled composition.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present disclosure typically include at most 80% by weight, more typically at most 70% by weight, and most typically at most 60% by weight ethylenically unsaturated compounds with acid functionality, based on the total weight of the unfilled composition.

Other Additives

Optionally, compositions of the present disclosure may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof.

Compositions of the present disclosure may further include core-shell polymer compounds. A core-shell compound includes a soft core comprising a rubber or elastomeric polymer surrounded by a shell comprising a more rigid polymer. Such compounds may reduce the shrinkage of the composition on polymerization. Exemplary core-shell polymer compounds are discussed in U.S. Publication No. 2005/0124762. (Cohen et al.).

If desired, the compositions of the disclosure may contain additives such as indicators, dyes (including photobleachable dyes), inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the hardenable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combination of any of the above additives may also be employed. The selection and amount of any one such additive can be selected by one of skill in the art to accomplish the desired result without undue experimentation.

Exemplary Composition of the Polymeric Layer Disposed on the Ceramic Material & Spherical Microparticles Suitable hardenable compositions for use in the polymeric layer disposed on the ceramic material (i.e., the basecoat) typically include a polymerizable component, a photoinitiator, a thermal initiator, a nanofiller, a pigment, and a filler. Particularly suitable polymerizable components for use in the basecoat include UDMA, phenoxyethylmethacrylate, and combinations thereof. Hardenable compositions coated on wall surfaces below the height of contour preferably include at least one flexible monomer or multimethacrylate oligomer. For basecoat hardenable compositions of the present disclosure that include fillers (nanofillers & other fillers) the compositions may include at least 1% by weight, more preferably at least 2% by weight, and most preferably at least 5% by weight filler, based on the total weight of the composition. For such embodiments, compositions of the present invention preferably include at most 75% by weight, more preferably at most 65% by weight, and even more preferably at most 55% by weight filler, based on the total weight of the composition.

Preparation of Polymer Compositions

The polymer compositions useful in the abrasion resistant hybrid coating of the present disclosure can be prepared by combining all the various components using conventional mixing techniques. The resulting composition may optionally contain fillers, solvents, water, and other additives as described herein. Typically, photopolymerizable compositions of the disclosure are prepared by simply admixing, under "safe light" conditions, the components of the inventive compositions. Suitable inert solvents may be employed if desired when affecting this mixture. Any solvent may be used which does not react appreciably with the components of the inventive compositions. Examples of suitable solvents include acetone, dichloromethane, isopropyl alcohol, ethanol, and butanone.

The amounts and types of each ingredient in the polymer compositions may be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and the loading and particle size distribution of filler(s). Such adjustments typically are carried out empirically based on previous experience with dental materials.

The components of the composition can be included in a kit, where the contents of the composition are packaged to allow for storage of the components until they are needed.

Coating the Dental Article

Prior to depositing the abrasion resistant hybrid coating, the target surface(s) (i.e., the portion of the article to be coated) of the dental article may be primed (e.g., abraded, etched, particles deposited) to enhance the bond between the coating and the metal substrate surface. In one embodiment, the target surfaces may be first sandblasted as known in the art by, for example, the method shown in U.S. Pat. No. 5,024,711 to Gasser et al. The target surfaces may be microblasted with an aluminum oxide sand, such as ROCATEC Pre, available from 3M ESPE. In some embodiments, the target surface may be subsequently treated with a silica-modified aluminum oxide, such as ROCATEC Plus, also available from 3M ESPE. Alternatively, the outer surface may be treated with ROCATEC Plus or other silica-modified aluminum oxide without prior treatment with ROCATEC Pre.

In another embodiment, the target surface of the dental article is primed or otherwise modified by etching with a strong acid such as hydrochloric acid. Additional useful etchants include nitric acids, hydrofluoric acids, ferric chlorides, sodium hydroxides, and combinations thereof. Although not wishing to be bound by theory, the roughening (i.e., priming) of the target surface by acid-etch or sandblast creates greater surface area and may strengthen the abrasion resistant hybrid coating bond to the chosen metal substrate.

The target surface may also be coated with a diamond-like glass (DLG), such as those described in U.S. Pat. No. 6,696,157 to David et al, as part of the priming process. DLG is an amorphous carbon system including a substantial quantity of silicon and oxygen that exhibits diamond-like properties. DLG may be deposited onto at least a portion of the target surface by plasma deposition or other techniques known to those having skill in the art.

Once the target surface of the dental article has been primed, the ceramic material may be deposited according to methods well known in the art, including, but not limited to, plasma spraying (i.e., thermal spraying), and powder coating followed by sintering. The ceramic material is directly bonded, by e.g., an intimate chemical or mechanical interaction, to the target surface. In certain preferred embodiments, the ceramic layer is made to include a smooth surface by, for example, using higher temperatures & smaller colloidal particles in the plasma spray. In one embodiment, the ceramic layer is deposited after priming and silanization and/or treatment with Zirconate as described below. In embodiments wherein a discontinuous ceramic layer is contemplated, the pattern (e.g., alternating gaps & ceramic deposits) may be created during the ceramic application (by e.g. lithography, masking) or after application of the ceramic layer (by e.g., laser ablation). For example, a curable resin can be applied in a grid, or waffle, pattern by a printing process. A layer of ceramic deposited on top of this pre-applied pattern, by thermal spraying, sputtering, or a similar process, will conform to the pre-existing pattern, creating a similar patterned structure on the surface of the dental article.

Alternatively, a thermally-sprayed layer of ceramic can be applied through a metal mask containing apertures in a pattern to be replicated on the underlying substrate. The mask may be disposed between the plasma spray mechanism and the dental article. The ceramic material may then be sprayed through the apertures, leaving portions of the outer surface uncoated and accordingly forming a discontinuous ceramic layer. Only that portion of the spray passing through the mask will actually deposit on the surface of the dental article.

Additionally or alternatively, the pattern or porosity may be created by subsequent laser ablation or sandblasting of targeted portions of the deposited ceramic layer. The laser used for converting (e.g., perforating or cutting) the ceramic layer article may be any suitable conventional laser. While many laser types may be suitable for the ablating of the ceramic coated articles described herein, high density gain media lasers such as solid state lasers, are particularly preferred. High density gain media lasers can span the infrared to the ultraviolet portion of the light spectrum, and also offer high peak power and high continuous power. Theses lasers can be composed of two types of gain media: insulators (e.g., Nd:YAG to Ti:Sapphire) and semiconductor (e.g., GaAs to Lead Salt). One preferred example of this type of laser is Nd:YVO$_4$ or neodymium-doped yttrium vanadate laser, and its shorter wavelength harmonics.

An additional bonding layer may be deposited on the ceramic layer and/or the surface of the dental article once the ceramic material has been deposited on the target surface. The ceramic coated dental article may undergo silanization by, for example, spray or bath after the sandblast or acid-etch abrasion procedure. Exemplary useful silanes include, but are not limited to, 3M ESPE Sil, available from 3M ESPE and methacryloxypropyltrimethoxy silane, available under the tradename GENIOSIL GF-31, from Wacker Chemical, Adrian, Mich. Alternatively or additionally, the primed dental article may be exposed (e.g., by spray or bath) to Zirconate coupling agents available from Kenrich Petrochemicals, Bayonne, N.J.

If a hardenable composition includes phosphorylated monomers, it may be unnecessary to include a bonding layer on the target surface of the dental article/ceramic layer after priming.

The first layer of hardenable composition can be applied using conventional techniques, including, but not limited to, dip coating, spray coating, spin coating, brush coating, and lithographic printing.

Thickness gradients and occlusal coatings may be created, for example, by directional spraying only the targeted portion of the crown with ceramic, hardenable composition, or combination of the two so that substantially none of a particular coating is applied below the height of contour. Use of the spherical microparticles on substantially only the occlusal surface may also create a gradient.

In preferred embodiments, the hardenable composition is deposited on the ceramic layer prior to curing. In embodiments wherein the hardenable composition includes a photoinitiator, a curing light, such as a VISILUX Model 2500 blue light gun (3M Co., St. Paul, Minn.) or a ELIPAR Freelight 2 LED CuringLight (available from 3M ESPE Dental Products, St. Paul, Minn.) is generally required to irradiate the hardenable compositions and initiate hardening (i.e., polymerization). Alternatively, an irradiating chamber may be used, such as a VISIO Beta Vario Light Curing Unit (available from 3M ESPE Dental Products, St. Paul, Minn.

In embodiments wherein the hardenable composition comprises a thermal initiator, heat may be used to initiate the hardening of free radically active groups. Examples of heat sources suitable for curing include inductive, convective, and radiant heat sources. Thermal sources should be capable of generating temperatures of at least 40° C. and at most 150° C. under normal conditions or at elevated pressure.

In certain embodiments wherein the hardenable composition comprises a photoinitiator and a thermal initiator, the curing process includes both irradiation and exposure to heat.

The spherical microparticles, can be added in any manner known to those skilled in the art for adding particles to a polymeric layer. The spherical microparticles can be mixed into a wet (i.e., at least partially uncured) coating or scattered on top of a wet coating. For example, the spherical microparticles can be applied by a pellet dispenser which applies or sprinkles the microparticles on top of a polymeric layer which is still at least partially uncured. Without wishing to be bound by theory, the microparticles may adhere to the at least partially uncured layer and at least a portion of the microparticles may "sink" into the layer.

Several types of scattering machines can be used to accomplish the uniform sprinkling or dispensing of microparticles. In certain embodiments, the scattering machine has a rotating or applicator roll (engraved or knurled) at the bottom of the hopper. A stationary or rotary brush is used to remove microparticles particles from the dispensing or applicator roll. A shaker screen may be used under the hopper for uniform distribution of the microparticles. The knurl size, the dispensing or applicator roll speed, the brush position, the speed of the rotary brush, and the speed and the size of the shaker screen should all be selected based on the amount and the size of the microparticles to be used.

Additional layers of hardenable composition can be applied to the first hardenable composition and spherical microparticles surface using the conventional techniques discussed above. Once all desired layers of hardenable compositions have been deposited, each layer of hardenable composition are hardened to the extent possible (i.e., fully cured) according to techniques described above.

As noted above, the abrasion resistant hybrid coating of the present disclosure provides desirable aesthetic properties, such as close approximation of tooth color. The following parameters form the basis of the color determination of the coated dental article: Opacity value O: Measure of the transparency (0% is completely transparent, 100% is opaque), L*-value: Brightness (100: complete reflection; 0; no reflection); a*-value: Red-green shift (+a: red; −a: green); b*-value: yellow-blue shift (+b: yellow; −b: blue).

The L*-value of a coated dental article is preferably greater than 60, more preferably greater than 75, and even more preferably greater than 80. The abrasion resistant hybrid coating may also be tailored to the shades on the VITA shade guide. The a* value of a coated dental article is within the range of −3 to 13. The b* value of a coated dental article is within the range of 10 to 35.

In certain embodiments, the abrasion resistant coating can maintain desirable flexibility. One method of determining flexibility includes the bending of a 150 micron thick metal coupon around a mandrel. The metal coupon is preferably made of the same metal used on the outer surface of the dental article and includes a deposited abrasion resistant coating. Preferably, a coated coupon can bend 180 degrees around an 8 millimeter mandrel without cracking of the coating. More preferably, a coated coupon can bend around a 4 millimeter mandrel, and even more preferably a 2 millimeter mandrel without cracking of the coating.

In another embodiment of the disclosure, a crown or a plurality of crowns (potentially of varying sizes) may be provided in a kit with the components of the abrasion resistant hybrid coating. The crown(s) may preferably be provided in the kit pre-primed (i.e., the surface has been roughened according to techniques described below). The kit may further include ceramic material, spherical microparticles, and one or more hardenable dental compositions. The coating components may be provided separately or already deposited on the crown surface. Such a kit may allow a practitioner to tailor the particular location and aesthetics of the coating on the crown. The kit may also include other components including, but not limited to, cements, brushes, and other tools to apply the coatings.

Illustrative Embodiments

1. A method for coating a dental article comprising:
providing a body comprising a metal substrate;
depositing a ceramic material on at least a portion of the surface of the body, wherein said depositing forms a ceramic layer;
depositing at least one hardenable composition comprising a polymerizable component on at least a portion of the ceramic layer, wherein depositing at least one hardenable composition forms a first polymeric layer; and
depositing a plurality of microscale spherical particles on at least a portion of the first polymeric layer, wherein the plurality of ceramic particles are at least partially embedded in the first polymeric layer.
2. The method of embodiment 1 further comprising priming a surface of the body, wherein priming at least a portion of a surface comprises:
depositing a layer of diamond-like glass on at least a portion of the surface.
3. The method of embodiment 1, further comprising priming a surface of the body, wherein priming a surface comprises:
exposing at least a portion of the surface to a strong acid or sandblasting at least a portion of the surface.
4. The method of any one of embodiments 1 to 3, further comprising applying a bonding layer to at least a portion of the outer surface, wherein the bonding layer is selected from the group consisting of silane and zirconate.
5. The method of embodiment 1, wherein depositing the ceramic layer comprises creating a continuous ceramic layer over at least a portion of the surface.
6. The method of embodiment 1, wherein the dental article is a stainless steel crown having a height of contour, and wherein the ceramic material is deposited substantially above the height of contour.
7. The method of embodiments 1-4 and 6, wherein depositing the ceramic layer comprises forming a discontinuous ceramic layer.
8. The method of embodiment 7, wherein the medical article is a stainless steel crown having a height of contour and wherein forming a discontinuous ceramic layer comprises forming the discontinuous layer on the outer surface substantially above the height of contour.
9. The method of embodiment 7, wherein forming the discontinuous ceramic layer comprises ablating at least a portion of the ceramic layer.
10. The method of any one of embodiments 1-9, wherein the ceramic material is selected from the group consisting essentially of: alumina, zirconia, yttria, yttria-stabilized zirconia, porcelain, and combinations thereof.
11. The method of embodiments 1-10, wherein depositing the ceramic material comprises plasma spraying the ceramic material on a surface of the body.
12. The method of any of the preceding embodiments, wherein the spherical particles comprise inorganic particles.
13. The method of embodiments 1-12, wherein the average microparticle diameter is at least 5 microns and no greater than 200 microns.
14. The method of embodiment 13, wherein the average microparticle diameter is as least 50 microns and no greater than 100 microns.
15. The method of embodiments 1-14, wherein the combined thickness of the ceramic layer and the first polymeric layer is at least the average microparticle diameter.
16. The method of any one of the preceding embodiments, wherein the polymeric component comprises at least one (meth)acrylate monomer.
17. The method of embodiment 16, wherein the polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.
18. The method of embodiments 1-17, wherein at least one hardenable composition comprises an initiator system, filler, and a pigment, wherein the filler comprises a nanofiller.
19. The method of embodiment 18, wherein the initiator system comprises a photoinitiator and a thermal initiator.
20. The method of embodiments 18-19, wherein the filler is present at no greater than 55 weight percent by weight of the composition.
21. The method of embodiment 20, wherein the filler comprises a fumed silica particle.
22. The method of embodiments 18-21, wherein the pigment selected from the group consisting of titanium dioxide, iron oxide, and combinations thereof.
23. The method of embodiment 22, wherein the pigment is present at a weight of no greater than 55% by weight of the polymer.
24. The method of any of the previous embodiments, further comprising depositing one or more additional hardenable compositions.
25. The method of any of the previous embodiments, wherein the thickness of the coating at a cervical margin of the crown is less than the thickness of the coating on the occlusal surface.
26. The method of any one of the preceding embodiments, wherein the hardenable composition further comprises flexible monomers, multimethacyrlate oligomers, and combinations thereof.
27. The method of embodiment 1, further comprising
irradiating at least a portion of the surface; and
exposing at least a portion of the surface to heat.
28. A dental article comprising:
a crown having a height of contour;
an abrasion resistant coating on at least a portion of the crown, the coating layer comprising:

a ceramic layer comprising a ceramic material disposed on at least a portion of the outer surface of the crown;

at least one polymeric layer disposed on at least a portion of the ceramic layer, wherein the at least one polymeric layer comprises at least one hardened dental composition comprising at least one polymerizable component; and a plurality of spherical microparticles embedded within at least one polymeric layer.

29. The dental article of embodiment 28, wherein at least one of the ceramic material and spherical microparticles are disposed substantially above the height of contour.

30. The dental article of any one of embodiment 28-29, wherein the ceramic material is selected from a group consisting of alumina, zirconia, yttria, yttria-stabilized zirconia, porcelain, and combinations thereof.

31. The dental article of embodiments 28-30, wherein the ceramic layer is a discontinuous ceramic layer.

32. The dental article of embodiment 31, wherein the discontinuous ceramic layer extends over at least a portion of the occlusal surface substantially above the height of contour.

33. The dental article of embodiments 28-32, wherein the thickness of the ceramic layer is no greater than 151 microns.

34. The dental article of embodiments 28-33, wherein the spherical microparticles comprise inorganic microparticles.

35. The dental article of embodiments 28-34, wherein the inorganic particles are selected from a group consisting of alumina, zirconia, yttria, yttria-stabilized zirconia, porcelain, and combinations thereof.

36. The dental article of embodiments 28-35, wherein at least one spherical particle of the plurality of spherical particles is in contact with the surface of the crown.

37. The dental article of embodiments 28-36, wherein said spherical microparticles are present in an amount of from about 5% by weight to about 75% by weight, based on the weight of the coating layer.

38. The dental article of embodiment 37, wherein said spherical microparticles are present in an amount of from about 10% by weight to about 50% by weight, based on the weight of the coating layer.

39. The dental article of embodiments 28-37, wherein thickness of the coating is at least the average microparticle diameter.

40. The dental article of any one of the preceding embodiments, wherein the hardenable composition comprises an initiator system, filler, and a pigment.

41. The dental article of embodiment 40, wherein the polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

42. The dental article of embodiment 41, wherein the polymerizable component is selected from the group consisting of phenoxylethylmethacrylate, urethane dimethacrylate, and combinations thereof.

43. The dental article of any one of the previous embodiments, wherein the polymerizable component further comprises a core-shell polymer compound.

44. The dental article of embodiments 40-43, wherein the initiator system comprises a photoiniator and a thermal initiator.

45. The dental article of embodiments 40-44, wherein the filler is present at no greater than 20 weight percent by weight of the composition.

46. The dental article of embodiments 40-44, wherein the pigment is selected from the group consisting of titanium dioxide, iron oxide, and combinations thereof.

47. The dental article of embodiment 46, wherein the pigment is present at a weight of no greater than 55% by weight of the polymer.

48. The dental article of embodiment 40-44, wherein at least one hardened composition further comprises flexible monomers, multimethacyrlate oligomers, and combinations thereof.

49. The article of embodiments 28-48, wherein the abrasion resistant coating comprises a thickness gradient.

50. The article of embodiments 28-49, further comprising a diamond-like glass layer deposited on at least a portion of the outer surface.

51. The article of embodiment 28-50, further comprising a bonding layer deposited on at least a portion of the outer surface, wherein the bonding layer comprises a component selected from the group consisting of silane and zirconate.

52 A kit comprising:
 a crown
 a ceramic material; and
 at least one hardenable dental composition comprising a polymerizable component, an initiator system, a pigment, and filler; and
 a plurality of spherical microparticles; and
 at least one of a cement, a brush, and instructions for application of the ceramic material, spherical microparticle, and hardenable dental composition.

53. The kit of embodiment 52, wherein the stainless steel crown further comprises a diamond-like glass layer on at least a portion of the outer surface.

54. The kit of embodiments 52 or 53, wherein the ceramic composition comprises a ceramic chosen from the group consisting of alumina, zirconia, yttria, yttria-stabilized zirconia, porcelain, and combinations thereof.

55. The kit of embodiments 52-54, wherein the polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

56. The kit of embodiments 52-55, wherein the bonding layer is selected from the group consisting of silane and zirconate.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:
1. A dental article comprising:
 a crown having a height of contour;
 an abrasion resistant coating on at least a portion of the crown, the coating layer comprising:
  a ceramic layer comprising a ceramic material disposed on at least a portion of the outer surface of the crown;
  at least one polymeric layer disposed on the entire ceramic layer, wherein the at least one polymeric layer comprises at least one hardened dental composition comprising at least one polymerizable component; and a plurality of spherical microparticles embedded within at least one polymeric layer;

wherein the dental article is malleable.

2. The dental article of claim 1, wherein at least one of the ceramic material and spherical microparticles are disposed substantially above the height of contour.

3. The dental article of claim 1, wherein the ceramic material is selected from a group consisting of alumina, zirconia, yttria, yttria-stabilized zirconia, porcelain, and combinations thereof.

4. The dental article of claim 1, wherein the ceramic layer is a discontinuous ceramic layer.

5. The dental article of claim 4, wherein the discontinuous ceramic layer extends over at least a portion of the occlusal surface substantially above the height of contour.

6. The dental article of claim 1, wherein the thickness of the ceramic layer is no greater than 151 microns.

7. The dental article of claim 1, wherein the microparticles are selected from a group consisting of alumina, zirconia, yttria, yttria-stabilized zirconia, porcelain, and combinations thereof.

8. The dental article of claim 1, wherein the polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

9. The article of claim 1, wherein the abrasion resistant coating comprises a thickness gradient.

* * * * *

UNITED STATES PATENT AND TRADEMARK OFFICE
CERTIFICATE OF CORRECTION

| | | |
|---|---|---|
| PATENT NO. | : 9,044,292 B2 | Page 1 of 1 |
| APPLICATION NO. | : 13/814962 | |
| DATED | : June 2, 2015 | |
| INVENTOR(S) | : Bhaskar Velamakanni | |

It is certified that error appears in the above-identified patent and that said Letters Patent is hereby corrected as shown below:

Title Page 2, Column 2 Under References Cited (Other Publications) Item (56):
Line 4, Delete "Matathesis" and insert -- Metathesis --, therefor.

In the specification

Column 9
Line 48, Delete "B-A." and insert -- $B-A_n$. --, therefor.
Line 50, Delete "B-A." and insert -- $B-A_n$. --, therefor.

Column 13
Line 33, Delete "Chemistr," and insert -- Chemistry, --, therefor.

Column 15
Line 3-4, Delete "andazobisisobutyronitrile" and insert -- azobisisobutyronitrile --, therefor.

Column 22
Line 29-30, Delete "phenoxoyethyl" and insert -- phenoxyethyl --, therefor.

In the claims

Column 23
Line 51, Delete "phenoxoyethyl" and insert -- phenoxyethyl --, therefor.
Line 63, Delete "photoiniator" and insert -- photoinitiator --, therefor.

Column 24
Line 38-39, Delete "phenoxoyethyl" and insert -- phenoxyethyl --, therefor.

Signed and Sealed this
Twenty-third Day of February, 2016

Michelle K. Lee
*Director of the United States Patent and Trademark Office*